United States Patent [19]

Snoble

[11] Patent Number: 4,655,975
[45] Date of Patent: Apr. 7, 1987

[54] SOLID CHELATING POLY(CARBOXYLATE AND/OR SULFONATE)PEROXYHYDRATE BLEACHES

[75] Inventor: Karel A. J. Snoble, Midland, Mich.

[73] Assignee: The Dow Chemical Company, Midland, Mich.

[21] Appl. No.: 822,992

[22] Filed: Jan. 27, 1986

[51] Int. Cl.$^4$ ............... C01B 15/055; C07C 59/305; C07C 143/04; D06L 3/02

[52] U.S. Cl. ........................ 260/503; 252/180; 252/181; 252/186.42; 252/186.43; 260/505 R; 260/505 C; 260/507 R; 260/512 R; 260/512 C; 260/513 R; 562/574; 562/578; 562/581; 562/582

[58] Field of Search ............ 252/180, 181, 186.42, 252/186.43; 260/503, 505 R, 505 C, 507 R, 512 R, 512 C, 513 R, 502 R; 562/574, 578, 581, 582

[56] References Cited

U.S. PATENT DOCUMENTS

| | | | |
|---|---|---|---|
| 3,055,897 | 9/1962 | Schwartz | 260/502 R |
| 3,394,172 | 7/1968 | Schiefer | 260/502.5 |
| 3,647,869 | 3/1972 | Kaloff | 562/584 |
| 3,691,139 | 9/1972 | Blumbergs | 525/327.8 |
| 3,897,347 | 7/1975 | Eckert | 252/8.75 |
| 3,929,875 | 12/1975 | Rapko | 252/99 |
| 3,954,500 | 5/1976 | Brown | 134/25 R |
| 4,021,376 | 5/1977 | Lamberti | 252/542 |
| 4,231,890 | 11/1980 | Yagi | 252/186 |
| 4,279,769 | 7/1981 | Yagi | 252/186 |

FOREIGN PATENT DOCUMENTS 2219150 8/1974 France .

Primary Examiner—Dennis L. Albrecht

[57] ABSTRACT

Polycarboxylates such as disodium diglycolate can form peroxyhydrates becoming a solid source of hydrogen peroxide. Upon dissolution in water, these poly(carboxylates and/or sulfonates) both form a chelant and hydrogen peroxide. This combination is particularly useful to form aqueous cleaning solutions for use in cleaning laundry, dishes and the like.

20 Claims, No Drawings

SOLID CHELATING POLY(CARBOXYLATE AND/OR SULFONATE)PEROXYHYDRATE BLEACHES

BACKGROUND OF THE INVENTION

This invention relates to solid peroxide bleaches.

Solid peroxide bleaches are useful soap and detergent additives. They are also useful in bleaching wood pulp.

Hydrogen peroxide is a useful bleach. It advantageously does not form chlorine as do many bleaches. Hydrogen peroxide is a liquid under ambient conditions. It generally is used and stored in the form of aqueous solutions. Concentrated aqueous solutions of hydrogen peroxide and hydrogen peroxide itself are fire and explosion hazards upon contamination with organic matter and/or certain metals. It is therefore desirable to have non-combustible hydrogen peroxide-containing solids which release hydrogen peroxide upon addition of the solid to water. It would be desirable if the entire solid was useful in the aqueous solution made from the solid.

SUMMARY OF THE INVENTION

The present invention is a solid poly(carboxylate and/or sulfonate) peroxyhydrate. The poly(carboxylate and/or sulfonate) is a salt comprising an organic polyanion and one or more cations. The organic anion is two or more carboxylate and/or sulfonate moieties joined by a moiety in which (1) each pair of carboxylate and/or sulfonate moieties are separated by a chain interrupted by one or more divalent moieties independently selected from the group —O—, —S— and

and (2) each carboxylate and/or sulfonate moiety is bonded to a carbon atom, which is bonded to at least one hydrogen atom such that a solid poly(carboxylate and/or sulfonate) peroxyhydrate can be formed.

These solid poly(carboxylate and/or sulfonate) peroxyhydrates, upon mixing with water form aqueous chelating bleach solutions, useful in bleaching wood pulp, cleaning substrates such as laundry and dishes, disinfecting substrates, disinfecting cooling tower water, and the like. The poly(carboxylate and/or sulfonate) peroxyhydrate solid is also useful as a solid source of oxygen.

DETAILED DESCRIPTION OF ILLUSTRATIVE EMBODIMENTS

The solid poly(carboxylate and/or sulfonate) peroxyhydrates of this invention may have associated with the poly(carboxylate and/or sulfonate) any number of peroxide molecules such as 1, 2, 5/2, 0.98. Preferably, the poly(carboxylate and/or sulfonate) peroxyhydrate has 1 hydrogen peroxide molecule associated with each poly(carboxylate and/or sulfonate) molecule. The hydrogen peroxide molecules are associated with the poly(carboxylate and/or sulfonate) molecule in a similar manner as are waters of hydration. These solid poly(carboxylate and/or sulfonate) peroxyhydrates may also have any number of waters of hydration associated with the poly(carboxylate and/or sulfonate).

Preferably, no waters of hydration are associated with the poly(carboxylate and/or sulfonate) peroxyhydrate.

Preferably, the organic anion is one represented by the formula:

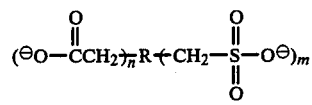

in which R is a n+m-valent radical provided that each radical between carboxylate and/or sulfonate moieties contains one or more moieties independently selected from the group —O—, —S— and

preferably —O—. Preferably, each chain is interrupted only once. R preferably contains from 0 to about 20 carbon atoms. R is preferably —O—, —CH$_2$—O—CH$_2$—,

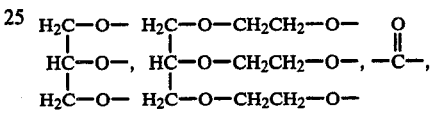

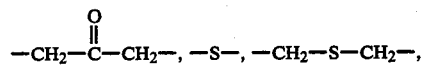

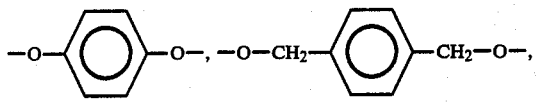

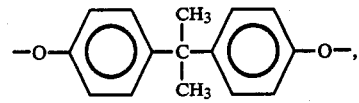

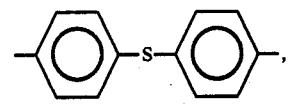

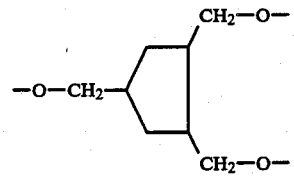

or —O—CH═CH—O—. More preferably, R is —CH$_2$—O—CH$_2$—, —O—,

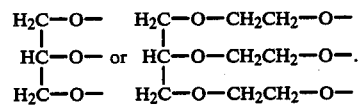

Most preferably R is —CH$_2$—O—CH$_2$—. n and m are independently positive integers. Preferably, m+n=2.

The cation can be any cation which allows the formation of the solid poly(carboxylate and/or sulfonate) peroxyhydrate. Preferably, each cation is independently selected from the group of the alkali metal cations; alkaline earth metal cation such as $Mg^{+2}$ and $Be^{+2}$; and ammonium cations. The ammonium cations are of the formula $R^1_4N^+$, in which $R^1$ is independently hydrogen or an organic moiety. Preferably, the cations are independently alkali metal cations, such as sodium, potassium and lithium; most preferably sodium. Preferably, the cations are the same.

The solid poly(carboxylate and/or sulfonate) peroxyhydrates of this invention may be formed by any suitable method. Preferred is precipitation from an aqueous solution comprising hydrogen peroxide and the carboxylate and/or sulfonate salt. Preferably, the hydrogen peroxide is in excess of the stoichiometric amount. More preferably, the hydrogen peroxide is in about two-fold excess of the stoichiometric amount. The precipitation may be driven by change in temperature of the aqueous solution, addition, formation or release of hydrogen peroxide and/or the carboxylate and/or sulfonate salt, evaporation of the water and the like. Preferably, the precipitation is driven by a decrease in the temperature of the aqueous solution, more referably, by less than about 20° C. temperature decrease. While the precipitation of poly(carboxylate and/or sulfonate) peroxyhydrate may occur at elevated or reduced pressures, it is preferred to occur at ambient pressures. Typical temperatures are between about 0° C. and about 25° C. Typical pressures are between about 0.005 and about 100 psig. The precipitation typically takes between 0 and about 120 minutes.

The poly(carboxylate and/or sulfonate) peroxyhydrate of this invention may be used by adding them to aqueous solutions to form solutions with the desired levels of polycarboxylates and/or hydrogen peroxide. Preferred are conventional levels. For example, in laundry cleaning solutions, preferred hydrogen peroxide levels generate between about 5 and about 40 ppm available oxygen. In wood pulp bleaching, preferred levels of hydrogen peroxide in the bleach liquor are between about 6 and about 26 g/liter. Alternatively, when used as a solid oxygen source, the solid poly(carboxylate and/or sulfonate) peroxyhydrate is heated dry to evolve oxygen. Preferably temperatures are between about 25° C. and about 100° C.

This invention is further illustrated by the following example.

EXAMPLE

Into an open, small flask is placed 0.004 liter of a 32 weight percent aqueous hydrogen peroxide solution (0.0418 mole). Disodium diglycolate monohydrate (4.31 g, 0.0219 mole) is added to the hydrogen peroxide solution as the solution is stirred. A colorless solution is obtained, which is cooled to 10° C. to precipitate a white crystalline mass. This mass is suction filtered and air dried for 30 minutes to yield 3.11 g. Iodometric titration shows $1.68 \times 10^{-3}$ mole of $H_2O_2$ in 0.439 g of product, which is consistent with a product of the formula

$NaOCCH_2OCH_2CONa.2.5H_2O_2$.

A 0.317-g sample of the air dried product is subjected to a vacuum of about 0.0005 millimeters of mercury for about 90 minutes at a temperature of 20° C. to yield a white crystalline solid with an iodometric titration consistent with the formula

$NaOCCH_2OCH_2CONa.H_2O_2$.

A 0.68-g sample of this vacuum dried product is placed in 2.03 ml of water and is water-soluble at 31° C.

I claim:

1. A solid poly(carboxylate and/or sulfonate) peroxyhydrate comprising a poly(carboxylate and/or sulfonate) salt containing an organic anion and one or more cations, said organic anion having two or more carboxylate and/or sulfonate moieties joined by a moiety in which (a) each pair of carboxylate and/or sulfonate moieties are separated by a polyvalent radical containing one or more moieties independently selected from the group —O—, —S— and

and (b) each carboxylate and/or sulfonate moiety is bonded to a carbon atom which is bonded to at least one hydrogen atom such that a solid poly(carboxylate and/or sulfonate) peroxyhydrate can be formed.

2. The solid poly(carboxylate and/or sulfonate) peroxyhydrate of claim 1 in which there are no waters of hydration.

3. The solid poly(carboxylate and/or sulfonate) peroxyhydrate of claim 1 in which there is 1 hydrogen peroxide molecule associated with each poly(carboxylate and/or sulfonate) molecule.

4. The solid poly(carboxylate and/or sulfonate) peroxyhydrate of claim 1 in which there is 5/2 hydrogen peroxide molecules associated with each poly(carboxylate and/or sulfonate) molecule.

5. The solid poly(carboxylate and/or sulfonate) peroxyhydrate of claim 1 in which the solid poly(carboxylate and/or sulfonate) peroxyhydrate is of the formula

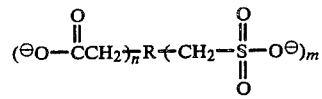

in hich R is a n+m-valent hydrocarbon radical provided that each chain between carboxylate and/or sulfonate moieties is interrupted by one or more moieties independently selected from the group —O—, —S— and

6. The solid poly(carboxylate and/or sulfonate) peroxyhydrate of claim 5 in which m+n=2.

7. The solid poly(carboxylate and/or sulfonate) peroxyhydrate of claim 5 in which each chain between carboxylate and/or sulfonate moieties is interrupted by one or more —O— moieties.

8. The solid poly(carboxylate and/or sulfonate) peroxyhydrate of claim 7 in which each chain is interrupted once.

9. The solid poly(carboxylate and/or sulfonate) peroxyhydrate of claim 5 in which R is selected from the group —O—, —CH$_2$—O—CH$_2$—,

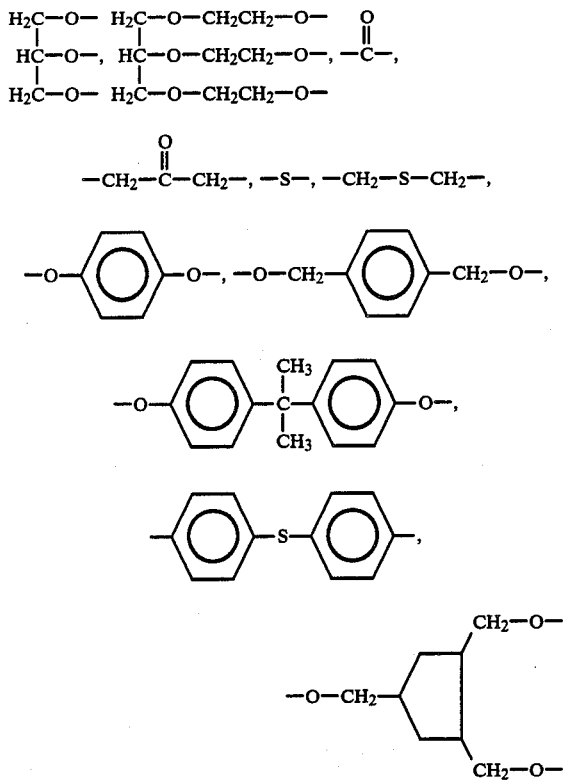

or —O—CH=CH—O—.

10. The solid poly(carboxylate and/or sulfonate) peroxyhydrate of claim 9 in which R is —CH$_2$—O—CH$_2$—.

11. The solid poly(carboxylate and/or sulfonate) peroxyhydrate of claim 1 in which each cation is independently an alkali metal cation, an alkaline earth cation, or an ammonium cation.

12. The solid poly(carboxylate and/or sulfonate) peroxyhydrate of claim 1 in which the cations are the same.

13. The solid poly(carboxylate and/or sulfonate) peroxyhydrate of claim 12 in which the cations are sodium.

14. The solid poly(carboxylate and/or sulfonate) peroxyhydrate of claim 12 in which the cations are potassium.

15. The solid poly(carboxylate and/or sulfonate) peroxyhydrate of claim 10 in which each cation is independently an alkali metal cation, an alkaline earth cation or an ammonium cation.

16. The solid poly(carboxylate and/or sulfonate) peroxyhydrate of claim 15 in which the cations are the same.

17. The solid poly(carboxylate and/or sulfonate) peroxyhydrate of claim 16 in which the cations are sodium.

18. The solid poly(carboxylate and/or sulfonate) peroxyhydrate of claim 16 in which the cations are potassium.

19. The solid poly(carboxylate and/or sulfonate) peroxyhydrate of claim 5 in which n=0.

20. The solid poly(carboxylate and/or sulfonate) peroxyhydrate of claim 5 in whic m=0.

* * * * *